(12) United States Patent
Haack et al.

(10) Patent No.: US 11,627,796 B2
(45) Date of Patent: Apr. 18, 2023

(54) CLEANING BRUSH

(71) Applicant: MICRO-TECH (NANJING) CO., LTD., Jiangsu (CN)

(72) Inventors: Scott Haack, Jiangsu (CN); Jianjun Shuang, Jiangsu (CN); Zhenghua Shen, Jiangsu (CN); Changqing Li, Jiangsu (CN); Minghao Feng, Jiangsu (CN)

(73) Assignee: Micro-Tech (Nanjing) Co., Ltd., Jiangsu (CN)

( * ) Notice: Subject to any disclaimer, the term of this patent is extended or adjusted under 35 U.S.C. 154(b) by 99 days.

(21) Appl. No.: 17/209,860

(22) Filed: Mar. 23, 2021

(65) Prior Publication Data

US 2021/0321755 A1    Oct. 21, 2021

(30) Foreign Application Priority Data

Mar. 24, 2020   (CN) .......................... 202020390679.0
Aug. 19, 2020   (CN) .......................... 202021742528.3

(51) Int. Cl.
  *B08B 9/043*   (2006.01)
  *A61B 90/70*   (2016.01)
  (Continued)

(52) U.S. Cl.
  CPC .......... *A46B 5/0004* (2013.01); *A46B 5/0037* (2013.01); *A46B 7/04* (2013.01);
  (Continued)

(58) Field of Classification Search
  CPC ... A46B 7/04; A46B 2200/3013; A61B 90/70; A61B 2090/701; B08B 9/0436; B08B 2209/04
  See application file for complete search history.

(56) References Cited

U.S. PATENT DOCUMENTS 6,088,866 A  *  7/2000  Hedge ..................... F41A 29/02
                                                   42/95
6,699,331 B1 *  3/2004  Kritzler .................. A61B 1/122
                                                   134/8
(Continued)

FOREIGN PATENT DOCUMENTS

KR   10-2006-0098205     *   9/2006
NZ           500521 A    *  11/2000
WO   WO 2006/123941 A1   *  11/2006

*Primary Examiner* — Randall E Chin
(74) *Attorney, Agent, or Firm* — K&L Gates LLP

(57) ABSTRACT

The disclosure provides a cleaning brush configured to clean a working channel of the endoscope. The cleaning brush comprises a first joint, a second joint and a plurality of cleaning units, the plurality of cleaning units are sequentially connected, each cleaning unit comprises a cleaning portion configured to be in contact with the working channel of the endoscope, and the hardness of the cleaning portions of at least two cleaning units in the plurality of cleaning units is different. The first joint and the second joint are respectively connected with two outermost cleaning units in the plurality of cleaning units, and the first joint and the second joint are configured to be connected to make a ring-shaped cleaning brush. The cleaning brush is efficient in removing bioburden from the working channel of an endoscope.

20 Claims, 6 Drawing Sheets

(51) Int. Cl.
*A46B 5/00* (2006.01)
*A46B 9/02* (2006.01)
*A46B 7/04* (2006.01)

(52) U.S. Cl.
CPC ............. *A46B 9/026* (2013.01); *A61B 90/70* (2016.02); *B08B 9/0436* (2013.01); *A46B 2200/3013* (2013.01); *A61B 2090/701* (2016.02); *B08B 2209/04* (2013.01)

(56) References Cited

U.S. PATENT DOCUMENTS

| | | | |
|---|---|---|---|
| 8,490,235 B2* | 7/2013 | Soetermans | B08B 9/0436 15/104.16 |
| 9,968,247 B2* | 5/2018 | Kaye | A61B 1/122 |
| 2010/0139018 A1* | 6/2010 | Maslanka | A61B 90/70 15/104.05 |
| 2010/0163074 A1* | 7/2010 | Hansen | A61B 90/70 134/8 |
| 2014/0123530 A1* | 5/2014 | Williams | B08B 9/0436 42/95 |
| 2016/0030984 A1* | 2/2016 | Rife | A61B 90/70 134/8 |
| 2017/0216890 A1* | 8/2017 | Seltz | A46B 3/18 |

* cited by examiner

CLEANING BRUSH

FIELD OF THE PRESENT DISCLOSURE

The disclosure relates to the technical field of endoscope cleaning, in particular to a cleaning brush.

BACKGROUND OF THE PRESENT DISCLOSURE

An endoscope is arranged with a working channel such that instruments like a cell brush, a snare, a foreign body net or grasper, a sclerotherapy needle or anything of the like can reach a pathological tissue through the working channel, and operations such as extracting the pathological tissue or injecting medicine liquid are carried out. When the instrument is drawn out of the working channel, bioburden tends to pollute the working channel such that the working channel needs to be cleaned appropriately after the endoscope is used.

Research finds that the existing cleaning brush for cleaning the working channel of the endoscope has the following disadvantages:

The cleaning effect is poor, and the cleaning efficiency is low.

SUMMARY OF THE PRESENT DISCLOSURE

An object of the present disclosure is, for example, to provide a cleaning brush capable of improving the cleaning effect and cleaning efficiency.

The embodiment of the disclosure is realized as follows.

The embodiment provides a cleaning brush configured to clean an endoscope working channel, comprising:

a first joint, a second joint and a plurality of cleaning units, wherein the plurality of cleaning units are sequentially connected, each cleaning unit comprises a cleaning portion configured to be in contact with the working channel of the endoscope, and at least two cleaning units have the cleaning portions of different hardness among the plurality of cleaning units; the first joint and the second joint are respectively connected with two outermost cleaning units in the plurality of cleaning units, and the first joint and the second joint are configured to be connected to make a ring-shaped cleaning brush.

In an alternative implementation, the cleaning portion is arranged as a bristle body, and the bristle bodies are different in hardness among at least two cleaning units.

In an alternative implementation, the number of the bristle bodies is multiple, and densities of a plurality of the bristle bodies of the at least two cleaning units are different.

In an alternative implementation, the outer diameters of the bristle bodies of the at least two cleaning units are different.

In an alternative implementation, at least two bristle bodies located in different cleaning units have different lengths.

In an alternative implementation, a plurality of bristle bodies in the same cleaning unit is equal in length.

In an alternative implementation, the cleaning unit further comprises a carrier, the carriers of the adjacent cleaning unit are connected, and the first joint and the second joint are respectively connected with two outermost carriers of the plurality of the carriers; the bristle body is connected with the carrier.

In an alternative implementation, the carriers of the adjacent cleaning unit are detachably connected.

In an alternative implementation, the carrier is a cable.

In an alternative implementation, the cleaning brush further comprises a hose or a catheter, and two cables of the adjacent cleaning unit are respectively inserted into two ends of the hose or the catheter.

In an alternative implementation, the first joint and the second joint are configured to be detachably connected.

In an alternative implementation, the first joint is arranged with a first connecting portion, and the second joint is arranged with a second connecting portion; one of the first connecting portion and the second connecting portion is arranged as a protrusion, the other is arranged as a groove, and the protrusion and the groove are configured to be in locking engagement.

In an alternative implementation, the groove has a lead-in section and a stop section which are communicated, one end of the stop section remote from the lead-in section extends to the end portion of the first joint or the end portion of the second joint, the protrusion is configured to enter the lead-in section and slide towards the stop section, and the protrusion resists the stop section so as to prevent the protrusion from separating from the stop section.

In an alternative implementation, the cleaning brush further comprises a wiping unit, and the wiping unit is connected with the cleaning unit.

In an alternative implementation, each of the plurality of cleaning units is located on one side of the wiping unit remote from the first joint or the second joint.

In an alternative implementation, the wiping unit comprises a wiping member and a connecting member, the connecting member is connected with the cleaning unit, and the wiping member is connected with the connecting member.

In an alternative implementation, the wiping member is an annular scraper arranged around the outer circumferential surface of the connecting member.

In an alternative implementation, the wiping member is arranged around the outer circumferential surface of a mount, and the outer circumferential surface of the wiping member is a taper surface.

In an alternative implementation, the wiping member is a helical scraper.

In an alternative implementation, the wiping member comprises a plurality of staggered wiper blades.

The embodiment of the disclosure has the beneficial effects as follows.

In summary, the embodiment provides a cleaning brush that comprises a plurality of cleaning units, each cleaning unit comprising a cleaning portion, and the hardness of the cleaning portions of at least two cleaning units being different, namely, the lodging resistance of the cleaning portions being different. Therefore, when the cleaning brush is used for cleaning the working channel of an endoscope, after the cleaning portion is contacted with the working channel of the endoscope, the cleaning portions with different hardness are pressed and deformed to different degrees after being contacted with the working channel of the endoscope such that the contact areas of the cleaning portions and the working channel of the endoscope are different, and the friction forces generated by the cleaning portions and the working channel of the endoscope in the relative sliding process are different. The cleaning portion with high hardness can separate foreign matters with strong adhesion force from the working channel of the endoscope, and then the cleaning portion with small hardness scrapes the foreign matters out of the working channel of the endoscope such that the foreign matters in the working channel of the endoscope can be comprehensively cleaned, and the cleaning effect and the cleaning efficiency are improved. Meanwhile, during cleaning, the first joint and the second joint can be connected such that the cleaning brush forms one annular structure, the cleaning brush can slide back and forth in the working channel of the endoscope, and the cleaning effect and the cleaning efficiency are improved.

BRIEF DESCRIPTION OF THE DRAWINGS

In order to more clearly illustrate the technical solution of the embodiment of the disclosure, the following drawings which are required to be used in the embodiment will be briefly described. It should be understood that the following drawings illustrate only some embodiments of the disclosure and are therefore not to be construed as limiting the scope thereof. For a person skilled in the art without involving any inventive effort, other related drawings may also be obtained from these drawings.

Figure 1:
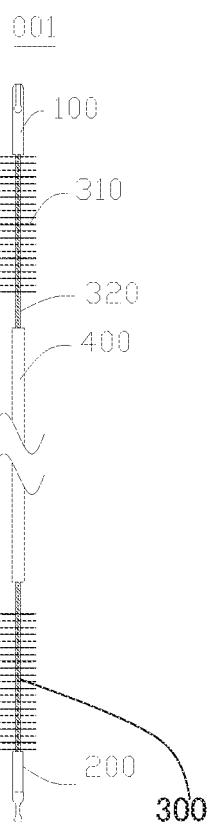
FIG. 1 is a schematic view showing a structure of a cleaning brush according to an embodiment of the disclosure.

List of reference numerals in the drawings:
001 cleaning brush
100 first joint
110 first insertion hole
120 groove
121 lead-in section
122 stop section
200 second joint
210 second insertion hole
220 protrusion
221 locking portion
222 avoiding portion
300 cleaning unit
310 cleaning portion
311 bristle body
320 carrier
400 flexible connecting member
500 wiping unit
510 wiping member
511 annular groove
520 connecting member

DESCRIPTION OF THE EMBODIMENTS

In order to make the objects, technical solutions and advantages of the embodiments of the disclosure clearer, the technical solutions of the embodiments of the disclosure will be clearly and completely described with reference to the drawings in the embodiments of the disclosure, and obviously, the described embodiments are part of the embodiments of the disclosure, not all embodiments. The assembly of the embodiments of the disclosure generally described and illustrated in the drawings herein may be placed and designed in a variety of different configurations.

Accordingly, the following detailed description of the embodiments of the disclosure provided in the accompanying drawings is not intended to limit the scope of the claimed disclosure, but merely represents selected embodiments of the disclosure. Based on the embodiments of the disclosure, all other embodiments obtained by a person of ordinary skills in the art without involving any inventive effort fall into the scope of the present disclosure.

It should be noted that: like numbers and letters refer to like items in the following drawings, and therefore, once an item is defined in one drawing, it need not be further defined and explained in subsequent drawings.

In the description of the present disclosure, it should be noted that the directional or positional relationships indicated by terms "center", "upper", "lower", "left", "right", "vertical", "horizontal", "inner", "outer" and the like are based on the directional or positional relationship shown in the drawings, or are directional or positional relationship in which the disclosure product is conventionally placed in use, and are merely for convenience in describing the disclosure and simplifying the description rather than indicating or implying that the device or element referred to must have a particular direction or be constructed and operated in a particular direction, and thus should not be construed as limiting the disclosure. Further, the terms "first", "second", "third" are used for distinguishing the description only and are not to be construed as indicating or implying the relative importance.

Further, the terms "horizontal", "vertical" and the like do not denote a requirement that the component should be absolutely horizontal or pendant, and slightly inclined may be allowed. For example, "horizontal" merely means that its direction is more horizontal than "vertical", and does not denote that the structure must be completely horizontal, but may be slightly inclined.

In the description of the disclosure, it should be noted that, unless otherwise clearly specified and defined, the terms "provided", "installed", "linked", "connected", etc. should be interpreted broadly, for example, a fixed connection, or a detachable connection, or an integral connection; a mechanical connection or an electrical connection; a direct connection or an indirect connection through an intermediate medium, and an interconnection between two elements. It will be understood by those of ordinary skills in the art that the specific meanings of the above terms in the present disclosure may be understood according to specific circumstances.

Referring to FIG. 1, the present embodiment provides a cleaning brush 001 for cleaning a working channel of an endoscope. The cleaning brush 001 has a good cleaning effect and high cleaning efficiency.

Figure 2:
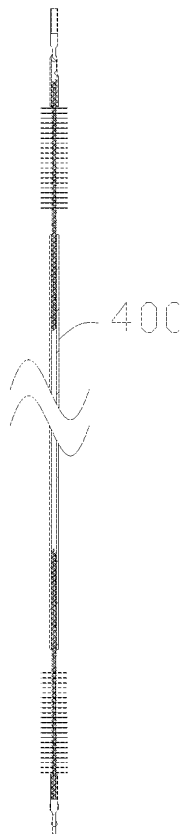
FIG. 2 is a schematic view showing a cross-sectional structure of a cleaning brush according to an embodiment of the disclosure.

Referring to FIG. 1 or FIG. 2, the cleaning brush 001 provided in this embodiment includes a first joint 100, a second joint 200, and a plurality of cleaning units 300 connected in sequence, each cleaning unit 300 including a cleaning portion 310 configured to be in contact with the working channel of an endoscope, and the hardness of the cleaning portions 310 of at least two of the plurality of cleaning units 300 being different. The first joint 100 and the second joint 200 are connected with two outermost cleaning units 300 of the plurality of cleaning units 300, respectively, and the first joint 100 and the second joint 200 are configured to be connected to make a ring-shaped cleaning brush 001.

In the embodiment, when the cleaning brush 001 is used for cleaning the working channel of the endoscope, cleaning liquid is introduced into the working channel first, then one end of the cleaning brush 001 penetrates into the working channel to ensure that the first joint 100 and the second joint 200 of the cleaning brush 001 are located outside the working channel, and then the first joint 100 and the second joint 200 are connected to enable the cleaning brush 001 to be in ring-shape. At this time, the pairing of the cleaning brush 001 with the endoscope is completed. In the cleaning process, the cleaning brush 001 is pulled so that the cleaning brush 001 slides back and forth relative to the working channel in the extending direction of the working channel. Obviously, when the cleaning brush 001 slides relative to the working channel, it is necessary to ensure that at least one cleaning unit 300 is located in the working channel so that the cleaning portion 310 can clean the inner wall of the working channel. Because the hardness of at least two cleaning portions 310 of the cleaning brush 001 provided by the embodiment is different, namely, the lodging resistance capabilities of the cleaning portions 310 are different, when the cleaning portion 310 is located in the working channel and is in contact with the inner wall of the working channel, the cleaning portions 310 with different hardness are pressed and deformed to different degrees after being in contact with the working channels of the endoscope such that the contact areas of the cleaning portions 310 and the working channel of the endoscope are different, and the friction forces generated between the cleaning portions 310 and the working channels of the endoscope in the relative sliding process are different. The cleaning portion 310 with strong hardness can separate foreign matters with strong adhesion force from the inner wall of the working channel, and then the cleaning portion 310 with small hardness scrapes the foreign matters out of the working channel of the endoscope along with the cleaning liquid such that the foreign matters like bioburden left in the working channel of the endoscope after a procedure can be removed, and the cleaning effect and the cleaning efficiency are improved. Meanwhile, in the cleaning process, the first joint 100 and the second joint 200 are connected such that the cleaning brush 001 forms one annular structure, the cleaning brush 001 is pulled to slide back and forth in the working channel of the endoscope, and the cleaning effect and the cleaning efficiency are improved.

It should be noted that the different hardness of the cleaning portions 310 may be generated by different materials of the cleaning portions 310, different outer diameters, or different array densities, etc.

Figure 3:
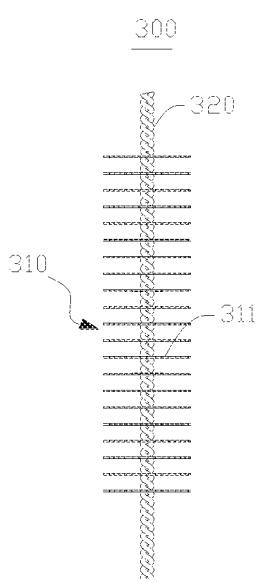
FIG. 3 is a schematic view showing a structure of a cleaning unit according to an embodiment of the disclosure.

Referring to FIG. 3, in this embodiment, alternatively, the cleaning unit 300 includes a carrier 320 and a bristle body 311 arranged as a cleaning portion 310, the bristle body 311 being connected with the carrier 320 and the carriers 320 of adjacent cleaning units 300 being connected.

Alternatively, the carrier 320 may be a cable braided from a plurality of steel wires. Obviously, the carrier 320 may be of other structures, which will not be enumerated in this embodiment.

Alternatively, the carriers 320 of adjacent cleaning units 300 can be detachably connected such that the number of cleaning unit 300 can be selected as required. The carriers 320 of a set number of cleaning units 300 can be sequentially connected, thereby obtaining cleaning brushes 001 of different lengths. When the first joint 100 and the second joint 200 are connected, the annular cleaning brushes 001 with different diameters can be formed such that the cleaning brush is used for cleaning the working channel with different lengths, and the application range is wide.

Referring to FIG. 1 or FIG. 2, alternatively, the cleaning brush 001 further includes a flexible connecting member 400, which may be a hose. It should be understood that the flexible connecting member 400 may be other flexible structures having a smooth outer circumferential surface. The adjacent carriers 320 are connected by one flexible connecting member 400, and the carrier 320 is detachably connected with the corresponding flexible connecting member 400, thereby realizing the detachable connection of the adjacent cleaning units 300.

It should be noted that the carrier 320 is connected with the flexible connecting member 400, the carrier 320 is inserted directly into the lumen of the flexible connecting member 400, and the carrier 320 may be detachably connected with the flexible connecting member 400 by snap connection or screw connection, etc.

In this embodiment, by providing the flexible connecting member 400, the part of the carrier 320 near the end portion thereof where the cleaning portion 310 is not provided can be inserted into the flexible connecting member 400. The length of the carrier 320 exposed outside the flexible connecting member 400 can be adjusted by controlling the depth of the carrier 320 inserted into the flexible connecting member 400. Specifically, the carrier 320 is inserted into the flexible connecting member 400 to a deep depth, and the distance between the flexible connecting member 400 and the adjacent cleaning portion 310 is short, that is, the length of the carrier 320 between the flexible connecting member 400 and the adjacent cleaning portion 310 is short. The length of the carrier 320 exposed to the external environment is short. When the cleaning brush 001 performs a cleaning operation, the probability that the carrier 320 is in contact with the inner wall of the working channel is reduced, and the carrier 320 is prevented from scraping the inner wall of the working channel such that the probability that the inner wall of the working channel is damaged is reduced, and the cleaning process is safe and reliable.

It should be noted that the part of the carrier 320 near the end portion thereof where the cleaning portion 310 is not provided may be inserted into the flexible connecting member 400 such that the cleaning portion 310 is substantially connected with the flexible connecting member 400.

It should be noted that the plurality of carriers 320 of the plurality of cleaning units 300 may be integrally formed, the plurality of carriers 320 being integrally formed, for example, the plurality of carriers 320 forming one complete cable, and the cleaning portions 310 of different cleaning units 300 are mounted on the cables.

It should be understood that, in other embodiments, a part of the carrier 320 on which the cleaning portion 310 is not mounted may be coated to make the surface of the carrier 320 smooth, which replaces solution of nesting the flexible connecting member 400 outside the carrier 320, thereby serving the same function of preventing the carrier 320 from scratching the inner wall of the working channel.

Alternatively, the number of the bristle body 311 of each cleaning unit 300 may be provided as required, for example, the bristle body 311 of each cleaning unit 300 may be one, or the number of bristle body 311 of each cleaning unit 300 may be multiple. In addition, the number of bristle body 311 of different cleaning units 300 may be different. When the number of the bristle body 311 is multiple, the multiple bristle bodies 311 are arranged around the outer circumferential surface of the carrier 320.

Alternatively, the bristle body 311 is an elongated strip, and the cross-sectional shape of the bristle body 311 may be circular. The cross section of the bristle body 311 refers to a plane perpendicular to the extending direction of the bristle body 311.

Alternatively, the hardness of the cleaning portions 310 of at least two cleaning units 300 may be different and may be, but is not limited to, one of the following:

the densities of the bristle bodies 311 of at least two cleaning units 300 are different;

the outer diameters of the bristle bodies 311 of least two cleaning units 300 are different;

the bristle bodies 311 of at least two cleaning units 300 are made of different materials; and at least two of the density, diameter and material of the bristle bodies 311 of at least two cleaning units 300 are different.

In this embodiment, it should be noted that a plurality of cleaning units 300 having a different hardness of the cleaning portion 310 may be disposed alternately.

In this embodiment, alternatively, the bristle bodies 311 of different cleaning units 300 have different lengths such that the cleaning effect of the cleaning brush 001 on the working channel of the endoscope can be improved.

It should be noted that when the number of the cleaning unit 300 is plural, the cleaning units 300 having different lengths are disposed alternately.

Further, alternatively, the bristle bodies 311 of the same cleaning unit 300 have the same length. For example, in the present embodiment, the number of the cleaning unit 300 is three, and the length of the bristle body 311 of the cleaning unit 300 located in the middle is longer than the lengths of the bristles of the cleaning unit 300 on two sides.

It should be noted that the length of the bristle body 311 extends in a direction perpendicular to the extending direction of the carrier 320.

In this embodiment, when the carrier 320 is a cable, the bristle body 311 is directly fixed to the cable during the braiding process of the cable.

Figure 4:
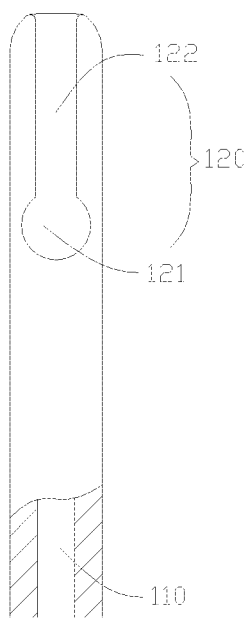
FIG. 4 is a schematic view showing a structure of a first joint according to an embodiment of the disclosure.

Referring to FIG. 4, in this embodiment, alternatively, one end of the first joint 100 is arranged with a first insertion hole 110, which may be a circular hole or a square hole, etc., configured for the insertion of the carrier 320. The outer wall of the first joint 100 is arranged with a groove 120. The groove 120 extends in the extending direction of the first joint 100, and one end of the groove 120 in the length direction thereof extends to the end face of the first joint 100 remote from the first insertion hole 110.

Alternatively, the groove 120 includes a lead-in section 121 and a stop section 122, the lead-in section 121 communicating with the stop section 122, and one end of the stop section 122 remote from the lead-in section 121 extending to the end surface of the first joint 100 remote from the first insertion hole 110. The lead-in section 121 is of an arc-shaped groove structure, the cross section of the stop section 122 is arc-shaped, the width of the notch of the stop section 122 is smaller than the width of the maximum notch of the lead-in section 121, and one end of the stop section 122 remote from the lead-in section 121 is provided as a necking.

Figure 5:
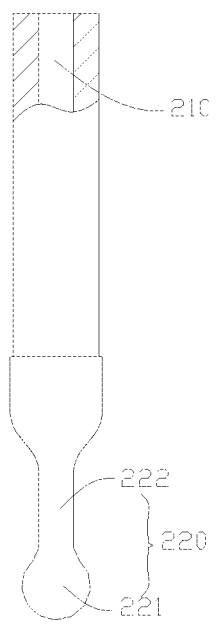
FIG. 5 is a schematic view showing a structure of a second joint according to an embodiment of the disclosure.

Referring to FIG. 5, alternatively, one end of the second joint 200 is arranged with a second insertion hole 210, which may be a square hole or a circular hole, configured for the insertion of the carrier 320. One end of the second joint 200 remote from the second insertion hole 210 is arranged with a protrusion 220, the protrusion 220 comprises a locking portion 221 and an avoiding portion 222, the locking portion 221 is spherical, the avoiding portion 222 is a cylindrical rod, and the outer diameter of the avoiding portion 222 is smaller than the diameter of the locking portion 221. The locking portion 221 is located at one end of the avoiding portion 222 remote from the first joint 100.

When the first joint 100 and the second joint 200 are connected, the locking portion 221 is aligned with the lead-in section 121, the avoiding portion 222 is aligned with the notch of the stop section 122, the locking portion 221 is nested into the lead-in section 121, and the avoiding portion 222 is located in the stop section 122. Then the first joint 100 and the second joint 200 are remote from each other. The locking portion 221 slides in the stop section 122 in a direction remote from the lead-in section 121 until the locking portion 221 slides to resist the necking end of the stop section 122 such that the locking portion 221 cannot be separated from one end of the stop section 122 remote from the lead-in section 121. The outer diameter of the locking portion 221 is larger than the width of the notch of the stop section 122 such that the locking portion 221 cannot be separated from the notch of the stop section 122 either. The assembly of the first joint 100 and the second joint 200 is completed. When disassembly is required, the first joint 100 and the second joint 200 are reversely operated to move the locking portion 221 to the lead-in section 121 and then it is taken out.

In other embodiments, the locking portion 221 may be provided in a spherical structure capable of being elastically deformed, and the inlet diameter of the lead-in section 121 is designed to be smaller than the maximum diameter of the lead-in section 121. When the first joint 100 and the second joint 200 are connected, the locking portion 221 is directly extruded into the lead-in section 121.

It should be noted that the first joint 100 may be provided with a groove 120 and, correspondingly, the second joint 200 may be provided with a protrusion 220.

It should be understood that the first joint 100 and the second joint 200 may also be other forms of detachably connected engaging structures.

Further, both the first joint 100 and the second joint 200 may be made of a flexible material, and the lengths of the first joint 100 and the second joint 200 are moderate so as to avoid the interference with the working channel when the first joint 100 and the second joint 200 are located in the working channel after the first joint 100 and the second joint 200 are paired, thereby preventing affecting the sliding of the cleaning brush 001 relative to the working channel.

Figure 6:
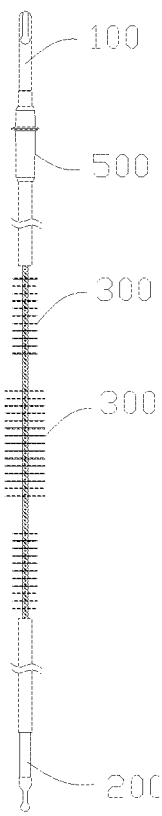
FIG. 6 is a schematic view showing a structure of a variation structure of a cleaning brush according to an embodiment of the disclosure.

Referring to FIG. 6, in this embodiment, alternatively, the cleaning brush 001 further includes a wiping unit 500 connected with the carrier 320.

It should be noted that the wiping member 510 may be mounted between adjacent carriers 320, or between the first joint 100 and the carrier 320 adjacent to the first joint 100, or between the second joint 200 and the carrier 320 adjacent to the second joint 200.

Alternatively, the wiping unit 500 includes a wiping member 510 and a connecting member 520 to which the wiping member 510 is connected.

Figure 7:
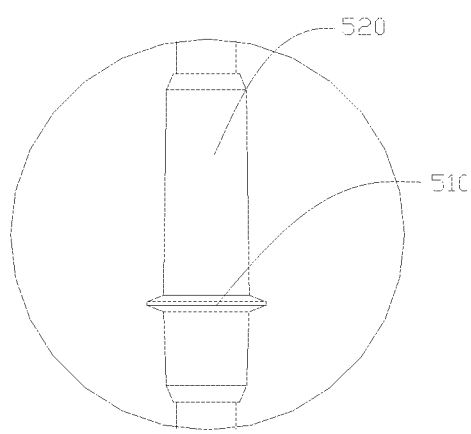
FIG. 7 is a schematic view showing a structure of a wiping unit according to an embodiment of the disclosure.

Referring to FIG. 7, alternatively, the wiping member 510 is arranged as an annular scraper that is fitted over the outer circumferential surface of the connecting member 520.

Alternatively, the wiping member 510 is arranged as a helical scraper, and the wiping member 510 extends helically around the axis of the connecting member 520 in the extending direction of the connecting member 520.

Figure 8:
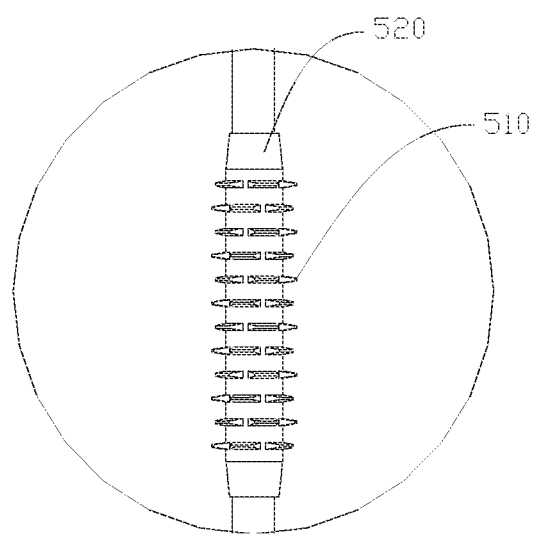
FIG. 8 is a schematic view showing a variation structure of a wiping unit according to an embodiment of the disclosure.

Referring to FIG. 8, alternatively, the wiping member 510 includes a plurality of staggered wiper blades.

Figure 9:
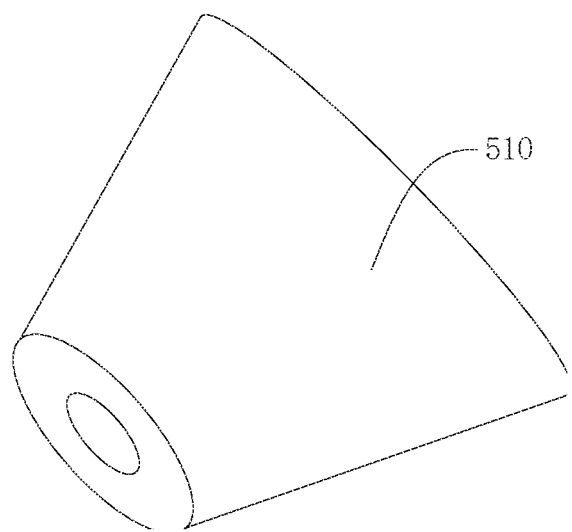
FIG. 9 is a schematic view showing another variation structure of a wiping unit according to an embodiment of the disclosure.

Alternatively, referring to FIG. 9, the wiping member 510 is arranged around the outside the connecting member 520, the outer circumferential surface of the wiping member 510 is a taper surface, and alternatively, the outer circumferential surface of the scraping member is a circular taper surface.

Figure 10:
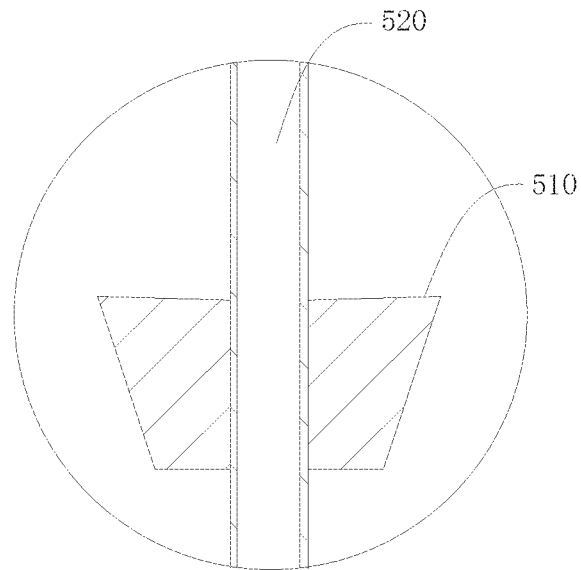
FIG. 10 is a schematic view showing a cross-sectional structure of a wiping unit according to an embodiment of the disclosure.

Referring to FIG. 10, it should be noted that the wiping member 510 is arranged with a through-hole which has a shape matched with the shape of the connecting member 520. For example, the through-hole may be a cylindrical hole, the wiping member 510 is sleeved outside the connecting member 520 by the through-hole, and the inner circumferential wall of the wiping member 510 is fitted to the outer circumferential surface of the connecting member 520.

Figure 11:
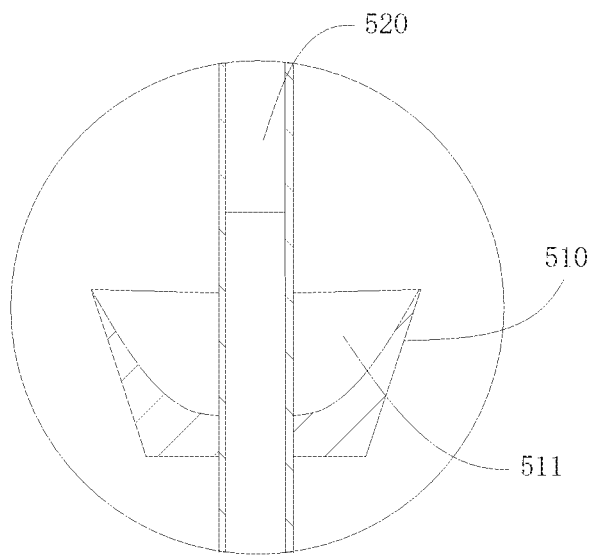
FIG. 11 is a schematic view showing a cross-sectional structure of another variation structure of a wiping unit according to an embodiment of the disclosure.

Referring to FIG. 11, alternatively, one end of the wiping member 510 having a large outer diameter is provided with an annular groove 511 communicated with the through-hole, and the circumferential groove wall of the annular groove 511 is spaced apart from the outer circumferential surface of the connecting member 520. The wiping member 510 is easily deformed during use so as to better fit the inner wall of the working channel.

Alternatively, the wiping member 510 is made of an elastic material, has a certain deformation capability, and can be better contacted with the inner wall of the working channel after being deformed, thereby improving the cleaning effect.

In this embodiment, the outer circumferential surface of the wiping member 510 is provided as a taper surface, and the outer diameter of the cross section of the wiping member 510 is gradually changed in the extending direction of the wiping member 510 so that the outer circumferential surface of the wiping member 510 can be in contact with the inner wall of the working channels with different inner diameter sizes, thereby expanding the application range. Meanwhile, the wiping member 510 has a small end and a large end. When the cleaning brush 001 is engaged with the endoscope working channel, the small end of the wiping member 510 can enter the working channel firstly such that the operation is more convenient.

Alternatively, the connecting member 520 is a flexible member, and the connecting member 520 has a certain elastic deformation capability and can yield to the working channel and bend along with the bending of the working channel, thereby facilitating the reciprocating sliding of the cleaning brush 001 in the working channel. For example, the connecting member 520 may be a hose.

Alternatively, the connecting member 520 is detachably connected with the carrier 320. The connecting member 520 is detachably connected with the first joint 100 or the second joint 200. When the connecting member 520 is connected with the carrier 320, the carrier 320 is directly inserted into the lumen of the connecting member 520, and the depth of inserting the carrier 320 into the connecting member 520 can be controlled such that the length of the carrier 320 between the connecting member 520 and the adjacent cleaning portion 310 is short, even zero, and the carrier 320 is prevented from damaging the inner wall of the working channel.

The present embodiment provides a cleaning brush 001 for cleaning the working channel of an endoscope. In use, one end of the cleaning brush 001 penetrates through the working channel and protrudes, and then the first joint 100 and the second joint 200 are connected so that the cleaning brush 001 forms an annular structure, and then at least one cleaning portion 310 is kept in the working channel. When the cleaning brush 001 is not arranged with a wiping member 510, the cleaning brush 001 can be repeatedly pulled so that the cleaning brush 001 slides back and forth in the extending direction of the working channel, and the inner wall of the working channel is cleaned by the cleaning portion 310. Since the hardness of the cleaning portions 310 is different, the cleaning effect and the cleaning efficiency are improved. When the cleaning brush 001 is arranged with the wiping member 510, the cleaning brush 001 can be operated to slide in one direction at this time, thereby simultaneously performing cleaning and wiping operations.

The above description is merely a preferred embodiment of the present disclosure and is not intended to limit the present disclosure. Various modifications and variations of the present disclosure will occur to those skilled in the art. Any modification, equivalent replacement, improvement, etc., made within the spirit and principle of the present disclosure shall be included in the scope of the present disclosure.

What is claimed is:

1. A cleaning brush configured to clean the working channel of an endoscope, characterized by comprising:
 a first joint, a second joint and a plurality of cleaning units, wherein the plurality of cleaning units are sequentially connected, each cleaning unit comprises a cleaning portion configured to be in contact with the working channel of the endoscope, and at least two cleaning units have the cleaning portions of different hardness among the plurality of cleaning units; the first joint and the second joint are respectively connected with two outermost cleaning units in the plurality of cleaning units, and the first joint and the second joint are configured to be connected with each other to make a ring-shaped cleaning brush.

2. The cleaning brush of claim 1, characterized in that the cleaning portion is arranged as a bristle body, and the bristle bodies are different in hardness among at least two cleaning units.

3. The cleaning brush of claim 2, characterized in that the number of the bristle bodies is multiple, and densities of a plurality of the bristle bodies of the at least two cleaning units are different.

4. The cleaning brush of claim 2, characterized in that outer diameters of the bristle bodies of the at least two cleaning units are different.

5. The cleaning brush of claim 2, characterized in that at least two said bristle bodies located in different cleaning units have different lengths.

6. The cleaning brush of claim 5, characterized in that a plurality of bristle bodies in the same cleaning unit are equal in length.

7. The cleaning brush of claim 2, characterized in that the cleaning unit further comprises a carrier, the carriers of the adjacent cleaning unit are connected, and the first joint and the second joint are respectively connected with two outermost carriers of the plurality of said carriers; the bristle body is connected with the carrier.

8. The cleaning brush of claim 7, characterized in that the carriers of the adjacent cleaning unit are detachably connected.

9. The cleaning brush of claim 7, characterized in that the carrier is a cable.

10. The cleaning brush of claim 9, characterized in that the cleaning brush further comprises a hose or a catheter, and two said cables of the adjacent cleaning unit are respectively inserted into two ends of the hose or the catheter.

11. The cleaning brush of claim 1, characterized in that the first joint and the second joint are configured to be detachably connected.

12. The cleaning brush of claim 11, characterized in that the first joint is arranged with a first connecting portion, and the second joint is arranged with a second connecting portion; one of the first connecting portion and the second connecting portion is arranged as a protrusion, the other is arranged as a groove, and the protrusion and the groove are configured to be in locking engagement.

13. The cleaning brush of claim 12, characterized in that the groove has a lead-in section and a stop section which are communicated, one end of the stop section remote from the lead-in section extends to an end portion of the first joint or the end portion of the second joint, the protrusion is configured to enter the lead-in section and slide towards the stop section, and the protrusion resists the stop section so as to prevent the protrusion from separating from the stop section.

14. The cleaning brush of claim 1, characterized in that the cleaning brush further comprises a wiping unit, and the wiping unit is connected with the cleaning unit.

15. The cleaning brush of claim 14, characterized in that each of the plurality of cleaning units is located on one side of the wiping unit remote from the first joint or the second joint.

16. The cleaning brush of claim 14, characterized in that the wiping unit comprises a wiping member and a connecting member, wherein the connecting member is connected with the cleaning unit, and the wiping member is connected with the connecting member.

17. The cleaning brush of claim 16, characterized in that the wiping member is an annular scraper arranged around an outer circumferential surface of the connecting member.

18. The cleaning brush of claim 16, characterized in that the wiping member is arranged around the outer circumferential surface of the connecting member, and the outer circumferential surface of the wiping member is a taper surface.

19. The cleaning brush of claim 16, characterized in that the wiping member is a helical scraper.

20. The cleaning brush of claim 16, characterized in that the wiping member comprises a plurality of staggered wiper blades.

\* \* \* \* \*